US010683478B1

(12) United States Patent
Ma et al.

(10) Patent No.: US 10,683,478 B1
(45) Date of Patent: Jun. 16, 2020

(54) DEVICE AND SYSTEM FOR PROCESSING A LIQUID SAMPLE CONTAINING CELLS

(71) Applicant: Shenzhen Eureka biotechnology Co. Ltd, Shenzhen, Guangdong (CN)

(72) Inventors: Mo Ma, Shenzhen (CN); Bofu Xue, Shenzhen (CN)

(*) Notice: Subject to any disclaimer, the term of this patent is extended or adjusted under 35 U.S.C. 154(b) by 0 days.

(21) Appl. No.: 16/414,652

(22) Filed: May 16, 2019

(51) Int. Cl.
*B04B 7/12* (2006.01)
*B04B 11/02* (2006.01)
*B04B 7/08* (2006.01)
*C12M 1/00* (2006.01)
*C12M 3/06* (2006.01)

(52) U.S. Cl.
CPC ............... *C12M 45/05* (2013.01); *B04B 7/08* (2013.01); *B04B 7/12* (2013.01); *B04B 11/02* (2013.01); *C12M 23/14* (2013.01); *C12M 23/16* (2013.01); *C12M 23/34* (2013.01)

(58) Field of Classification Search
CPC ......... B04B 11/04; B04B 11/02; B04B 15/08; B04B 7/08; B04B 7/12; C12M 45/05; C12M 23/14; C12M 23/34; C12M 23/16
USPC ......... 494/12, 83, 41, 38, 43, 84–85, 56, 36, 494/25–26, 67
See application file for complete search history.

(56) References Cited

U.S. PATENT DOCUMENTS

| | | | | |
|---|---|---|---|---|
| 3,409,213 A | * | 11/1968 | Latham, Jr. | ............... F16J 15/36 494/41 |
| 3,565,330 A | * | 2/1971 | Latham, Jr. | ........... B04B 5/0442 494/41 |
| 3,706,412 A | * | 12/1972 | Latham, Jr. | ............... B04B 7/00 494/7 |
| 3,785,549 A | * | 1/1974 | Latham, Jr. | ........... B04B 5/0442 494/43 |
| 4,140,268 A | * | 2/1979 | Lacour | ...................... B04B 7/00 494/41 |
| 4,300,717 A | * | 11/1981 | Latham, Jr. | ......... A61M 1/3693 277/399 |
| 4,684,361 A | * | 8/1987 | Feldman | ............... B04B 5/0442 277/353 |
| 4,692,136 A | * | 9/1987 | Feldman | ............... B04B 5/0442 277/353 |
| 4,767,396 A | * | 8/1988 | Powers | ................. B04B 5/0442 494/60 |

(Continued)

FOREIGN PATENT DOCUMENTS

| | | | | |
|---|---|---|---|---|
| EP | 3466542 A4 | * | 11/2019 | ........... B04B 5/0442 |
| JP | 59069166 A | * | 4/1984 | |
| JP | 09192215 A | * | 7/1997 | ........... A63M 1/3696 |

*Primary Examiner* — Charles Cooley
(74) *Attorney, Agent, or Firm* — Feng Qian

(57) ABSTRACT

A device for processing a liquid sample containing cells is provided. The device includes a stationary part and a rotatable part. The stationary part includes a cap, a socket connected to the cap, and a tube located within the cap and the socket. The rotatable part includes a centrifugal processing chamber, and a flow guide located within the centrifugal processing chamber. The stationary part and the rotatable part are connected by a plurality of rotary dynamic seals allowing rotation of the rotatable part relative to the stationary part. The cap includes a first port connected to an inlet, and a second port connected to an outlet. The centrifugal processing chamber includes an upper wall, a neck extending from the upper wall, a sidewall and a bottom wall tilting downwardly.

16 Claims, 14 Drawing Sheets

(56) References Cited

U.S. PATENT DOCUMENTS

| | | | | |
|---|---|---|---|---|
| 4,859,333 A * | 8/1989 | Panzani | ............... | A61M 1/3693 210/360.2 |
| 4,879,031 A * | 11/1989 | Panzani | ............... | B04B 5/0442 210/360.2 |
| 4,943,273 A * | 7/1990 | Pages | ............... | A61M 39/28 494/41 |
| 4,983,158 A * | 1/1991 | Headley | ............... | A61M 39/28 494/38 |
| 5,045,048 A * | 9/1991 | Kaleskas | ............... | B04B 5/0442 277/393 |
| 5,100,372 A * | 3/1992 | Headley | ............... | B04B 5/0442 494/38 |
| 5,141,486 A * | 8/1992 | Antwiler | ............... | A61M 1/3693 494/27 |
| 5,387,174 A * | 2/1995 | Rochat | ............... | B04B 5/0442 494/10 |
| 5,405,308 A * | 4/1995 | Headley | ............... | B04B 5/0407 494/41 |
| 5,514,070 A * | 5/1996 | Pages | ............... | B04B 5/0442 494/41 |
| 5,882,289 A * | 3/1999 | Sakota | ............... | B04B 5/0442 494/41 |
| 5,919,125 A * | 7/1999 | Berch | ............... | B04B 5/0442 494/41 |
| 6,352,499 B1 * | 3/2002 | Geigle | ............... | B04B 5/0442 494/37 |
| 6,464,624 B2 * | 10/2002 | Pages | ............... | B04B 5/0442 494/36 |
| 6,629,919 B2 * | 10/2003 | Egozy | ............... | B04B 5/0442 494/36 |
| 7,001,323 B2 * | 2/2006 | Panzani | ............... | A61M 1/0281 210/739 |
| 7,156,800 B2 * | 1/2007 | Panzani | ............... | A61M 1/0281 210/739 |
| 7,186,230 B2 * | 3/2007 | Briggs | ............... | A61M 1/3693 210/360.1 |
| 7,211,037 B2 * | 5/2007 | Briggs | ............... | A61K 41/0066 210/206 |
| 7,914,477 B2 * | 3/2011 | Briggs | ............... | A61K 41/0066 210/380.1 |
| 8,070,666 B2 * | 12/2011 | Rochat | ............... | B04B 5/0442 494/26 |
| 9,222,067 B2 * | 12/2015 | Kessler | ............... | C12M 47/02 |
| 9,308,314 B2 * | 4/2016 | Galavotti | ............... | B04B 5/0442 |
| 9,682,185 B2 * | 6/2017 | Brunner | ............... | B04B 5/0442 |
| 10,040,077 B1 * | 8/2018 | Sutton | ............... | B04B 11/02 |
| 10,293,097 B2 * | 5/2019 | Murphy | ............... | B04B 5/0442 |
| 10,384,216 B1 * | 8/2019 | Sutton | ............... | B04B 11/02 |
| 2001/0027156 A1 * | 10/2001 | Egozy | ............... | B04B 5/0442 494/37 |
| 2002/0032112 A1 * | 3/2002 | Pages | ............... | B04B 5/0442 494/36 |
| 2002/0142909 A1 * | 10/2002 | Sakota | ............... | A61M 1/3693 494/41 |
| 2003/0181305 A1 * | 9/2003 | Briggs | ............... | A61M 1/3693 494/37 |
| 2006/0199720 A1 * | 9/2006 | Juan | ............... | B04B 5/0442 494/41 |
| 2013/0089917 A1 * | 4/2013 | Kessler | ............... | C12M 47/02 435/261 |
| 2015/0284671 A1 * | 10/2015 | Kessler | ............... | C12M 47/02 435/308.1 |

* cited by examiner

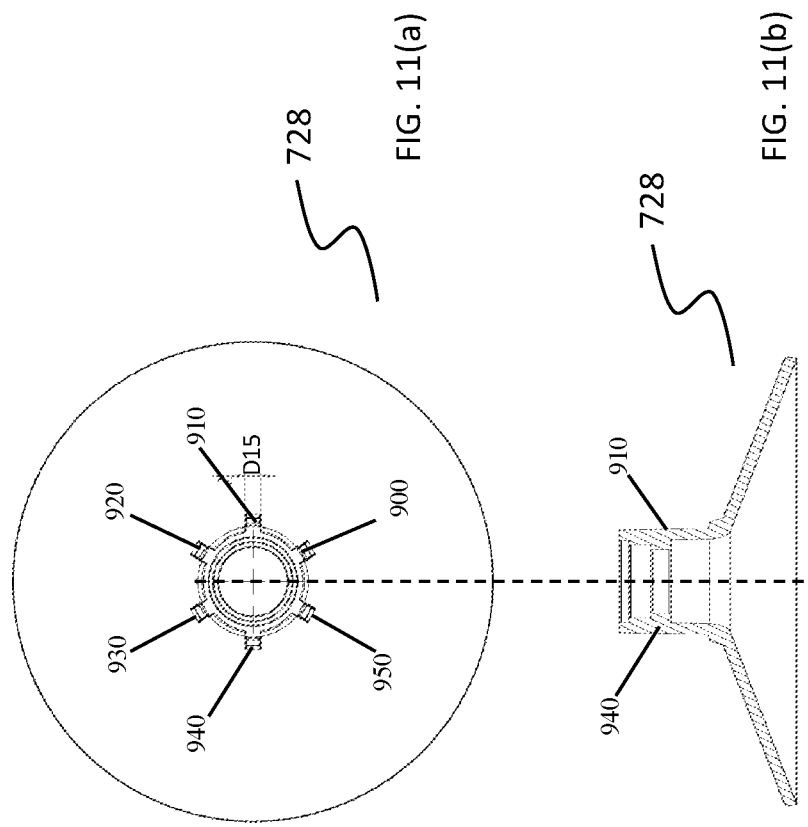

DEVICE AND SYSTEM FOR PROCESSING A LIQUID SAMPLE CONTAINING CELLS

FIELD OF THE DISCLOSURE

The present disclosure relates to a device and a system for processing a liquid sample containing cells.

BACKGROUND OF THE DISCLOSURE

The background description provided herein is for the purpose of generally presenting the context of the present disclosure. The subject matter discussed in the background of the present disclosure section should not be assumed to be prior art merely as a result of its mention in the background of the present disclosure section. Similarly, a problem mentioned in the background of the present disclosure section or associated with the subject matter of the background of the present disclosure section should not be assumed to have been previously recognized in the prior art. The subject matter in the background of the present disclosure section merely represents different approaches, which in and of themselves may also be disclosures. Work of the presently named inventors, to the extent it is described in the background of the present disclosure section, as well as aspects of the description that may not otherwise qualify as prior art at the time of filing, are neither expressly nor impliedly admitted as prior art against the present disclosure.

Processing cell-containing liquid samples includes separating biological fluid components from a biological fluid. For example, separating biological fluid components from a biological fluid may include separating biological cells from other medium in a cell fluid. In one example, a process of cell therapy may include a method that a part of cells is isolated and extracted from human and/or animal tissues or peripheral blood and then the processed cells are implanted into humans and/or animals, or modified and cultivated in vitro before implanted into humans and/or animals. The process in cell therapy may include the process of cell isolation, modification and cultivation in vitro. For example, during Chimeric Antigen Receptor T (CAR-T) cell preparation, the whole process may be divided into steps of peripheral blood collection; peripheral blood mononuclear cell (PBMC) separation; cell separation of one or more specific populations; cell activation; cell cultivation; viral transfection; cell multiplication; cell concentration; cell wash; solvent preparation; and/or cell implantation. Different cell preparation methods may have one or more different implementations based on different processes. The one or more different implementations mainly involve cell separation of one or more specific populations; cell activation; cell cultivation; and virus transfection.

Among the cell preparation processes, cell concentration may include the process of separating biological fluid components from a large volume of a biological fluid, down to a small volume. For example, the large volume of a biological fluid may be stored in a large cultivation system (e.g., from a few hundred milliliters to 20 liters) and a small volume may be implemented by a small solvent preparation system (e.g., usually 100-500 ml). The concentration ratio may be more than 10 times. Most of the clinical cell therapies may be operated in one or more closed systems. Specifically, the whole process from cell collection to cell implantation may be completed in a closed system. Thus, the biological fluid may be prevented from contacting with outside environment and the risk of pollution and cross-contamination is reduced. Therefore, how to separate biological fluid components from a large volume of a biological fluid, down to a small volume in a closed system is a critical technical aspect in the cell preparation process.

The current technology for cell concentration may be mainly divided into two methods. The first method is carried out by a centrifugal system. Through a barrel-shaped centrifugal device, a cell-containing liquid sample is pumped into a barrel, centrifuged, and the waste liquid is discharged. Then the sample is pumped into the barrel again, and the centrifugal process is repeated until the centrifugation and concentration processes of all the sample are finished. The disadvantage of the first method is that the concentration process is time-consuming. It usually takes several rounds of centrifugation, and each round takes about 3-20 minutes for cell concentration. Furthermore, the volume of centrifugal barrel is limited, so that only limited sample can be concentrated in each round. It usually takes about a number of hours, for example, 10 hours, to concentrate 10 liters of the sample. Meanwhile, the cell survival rate is seriously reduced by using this method. Therefore, the first method may not be suitable for cell liquid concentration with a large volume.

The second method is achieved by using hollow fiber or membrane filtration. The second method usually uses a membrane with uniform pore sizes. Under the effect of the tangential flow, the cells are throttled on one side of the membrane and the waste liquid passes through the membrane, and then the objective of cell concentration is achieved. However, how to control liquid pressure and liquid flow rate is important. If liquid pressure is increased and the liquid flow rate is kept constant, the cells may experience high pressure and the membrane system may be easily blocked. Thus, the concentration efficiency may be decreased, and the cell survival rate may be reduced. Conversely, if the liquid pressure is decreased, the cell concentration efficiency may be low. It may take a long time to concentrate the same volume of cell liquid. If the flow rate of the sample is increased, the concentration efficiency may be reduced. In the meantime, the cells may experience increasing friction and the cell survival rate may be reduced. If the flow rate is reduced, cells may be precipitated and the membrane surface may be blocked, thus the concentration efficiency may be gradually reduced.

Therefore, the methods of controlling liquid pressure and liquid flow rates are key points of the membrane filtration system. The efficiency of cell concentration can be improved by increasing the surface area of the membrane in the membrane filtration system. However, the larger the surface area of the membrane, the cost may be higher. Therefore, the second method may not be suitable for cell concentration.

Most of the cell preparation processes involves cell cultivation and multiplication in vitro, through which the biological fluid is concentrated from a large cultivation volume (e.g., from a few hundred milliliters to 20 liters) to a small solvent preparation volume (e.g., usually dozens to hundreds of milliliters) that can be implanted to the human body. Accordingly, how to concentrate a sample from a large cultivation system to a small solvent preparation system in a closed system remains a problem. In the process of cell concentration, a number of parameters such as cell recovery rate, cell survival rate, and time may be assessed. However, the current cell concentration method and device that utilized cannot satisfy the industry requirements for cell preparation.

In the meantime, the current technology of cell therapy often involves cells that are extracted from and implanted to the same object. It may be important to consider during cell preparation that how to produce drugs with a similar standard based on different cells from different patients; that is consistent cell preparation. The cell preparation process often uses one or more single disposable products; thus, the current systems of rapid concentration cannot meet the needs of cell preparations. Therefore, a heretofore unaddressed need exists in the art to address the aforementioned deficiencies and inadequacies.

SUMMARY OF THE DISCLOSURE

There is provided a device for processing a liquid sample containing cells. The device for processing a liquid sample containing cells comprises: a stationary part; and a rotatable part.

In one embodiment, the cells contained in the liquid sample may be any kind of cells, preferably mammalian cells, more preferably human cells.

In one embodiment, the stationary part includes a cap, a socket connected to the cap, and a tube located within the cap and the socket.

In one embodiment, the rotatable part includes a centrifugal processing chamber, and a flow guide located within the centrifugal processing chamber.

In one embodiment, the stationary part and the rotatable part are connected by a plurality of rotary dynamic seals allowing rotation of the rotatable part relative to the stationary part.

In one embodiment, the cap includes a first port connected to an inlet, and a second port connected to an outlet.

In one embodiment, the centrifugal processing chamber includes an upper wall, a neck extending upwardly from the upper wall, a sidewall and a bottom wall tilting downwardly.

In one embodiment, the neck includes an upper neck and a lower neck.

In one embodiment, a lowest point is formed in the middle of the bottom wall, so that the liquid in the centrifugal processing chamber is guided to the lowest point due to gravity.

In one embodiment, the flow guide is inserted in and coaxially rotatable with the centrifugal processing chamber during centrifugation.

In one embodiment, the flow guide is close to but not in contact with the upper wall of the centrifugal processing chamber.

In one embodiment, the flow guide is sized and shaped to fit the upper wall of the centrifugal processing chamber.

In one embodiment, the flow guide includes a center hole and the center hole is sized and shaped to fit the tube.

In one embodiment, the tube passes through the center hole.

In one embodiment, the upper end of the tube is connected to the outlet.

In one embodiment, the lower end of the tube is close to but not in contact with the lowest point, allowing that the liquid guided to the lowest point is removed from the centrifugal processing chamber.

In one embodiment, the device is configured to receive the liquid sample from the inlet and guide the liquid sample to flow through a first space between the cap and the tube, a second space between the upper neck and the tube, a third space between the lower neck and the tube, and a fourth space between the upper wall and the flow guide and to the side wall of centrifugal processing chamber in order.

In one embodiment, the upper end of the tube is fixed at the second port connected to the outlet.

In one embodiment, the device further comprises at least one stationary seal.

In one embodiment, the device further comprises a bearing connected to both the stationary part and the rotatable part.

In one embodiment, the flow guide includes a hollow upwardly-protruding central part connected to the center hole.

In one embodiment, a plurality of protrusions are provided on the sidewall of the upwardly-protruding central part.

In one embodiment, the plurality of protrusions are configured to fix the flow guide inside the neck of the centrifugal processing chamber.

In one embodiment, the device further comprises an inner dynamic seal disc located inside the upper end of the upwardly-protruding central part and connected with a location stop sleeve located at the outside wall of the tube by one of a plurality of rotary dynamic seals.

In one embodiment, a part for connecting a centrifugal driving device is provided on the bottom of the centrifugal processing chamber, enabling the rotation of the centrifugal processing chamber driven by the centrifugal driving device.

In one embodiment, the upper wall of the centrifugal processing chamber and the part of the flow guide in proximity to the upper wall are horizontal or inclined upwardly.

In one embodiment, the centrifugal processing chamber includes an upper part and a lower part connected to the upper part, and wherein the upper part includes the neck, the upper wall and the sidewall and the lower part includes the bottom wall tilting downwardly.

In one embodiment, the first port is connected to the inlet via a first connector and/or the second port is connected to the outlet via a second connector.

In one embodiment, the centrifugal processing chamber is rotational symmetric.

A system for processing a liquid sample containing cells is provided. The system includes the device for processing a liquid sample containing cells as described above, at least one sample bag/washing solution bag, at least one collection bag/waste bag, and a pipeline system for connecting the at least one sample bag/washing solution bag to the inlet of the device and connecting the at least one collection bag/waste bag to the outlet of the device. In one embodiment, the system further comprises a fluid driving device.

In one embodiment, the fluid driving device includes a first peristaltic pump connected to the inlet and/or a second peristaltic pump connected to the outlet.

A method for processing a liquid sample containing cells using the device for processing a liquid sample containing cells as described above is provided. The method comprises the following steps:

inputting the liquid sample to the device via the inlet during the centrifugal rotation of the centrifugal processing chamber; and outputting the processed liquid from the device via the tube and the outlet during or after the centrifugal rotation of the centrifugal processing chamber.

In one embodiment, the inputting and the outputting are simultaneous.

In one embodiment, the method further comprises:
filing the centrifugal processing chamber with a washing solution;

mixing the washing solution with the cells remaining in the centrifugal processing chamber by rotating the centrifugal processing chamber clockwise and counterclockwise; and outputting and collecting a mixture of the cells and the washing solution.

BRIEF DESCRIPTION OF THE DRAWINGS

The accompanying drawings illustrate one or more embodiments of the present disclosure and, together with the written description, serve to explain the principles of the present disclosure. Wherever possible, the same reference numbers are used throughout the drawings to refer to the same or like elements of an embodiment.

FIG. 11(*a*) is a plan view of the flow guide as shown in FIG. 9.

FIG. 11(*b*) is a cross-sectional view of the flow guide as shown in FIG. 9.

FIG. 12(*b*) is a perspective view of the inlet and the outlet of the device for processing cell-containing liquid samples as shown in FIG. 6.

DETAILED DESCRIPTION OF THE DISCLOSURE

Figure 1:
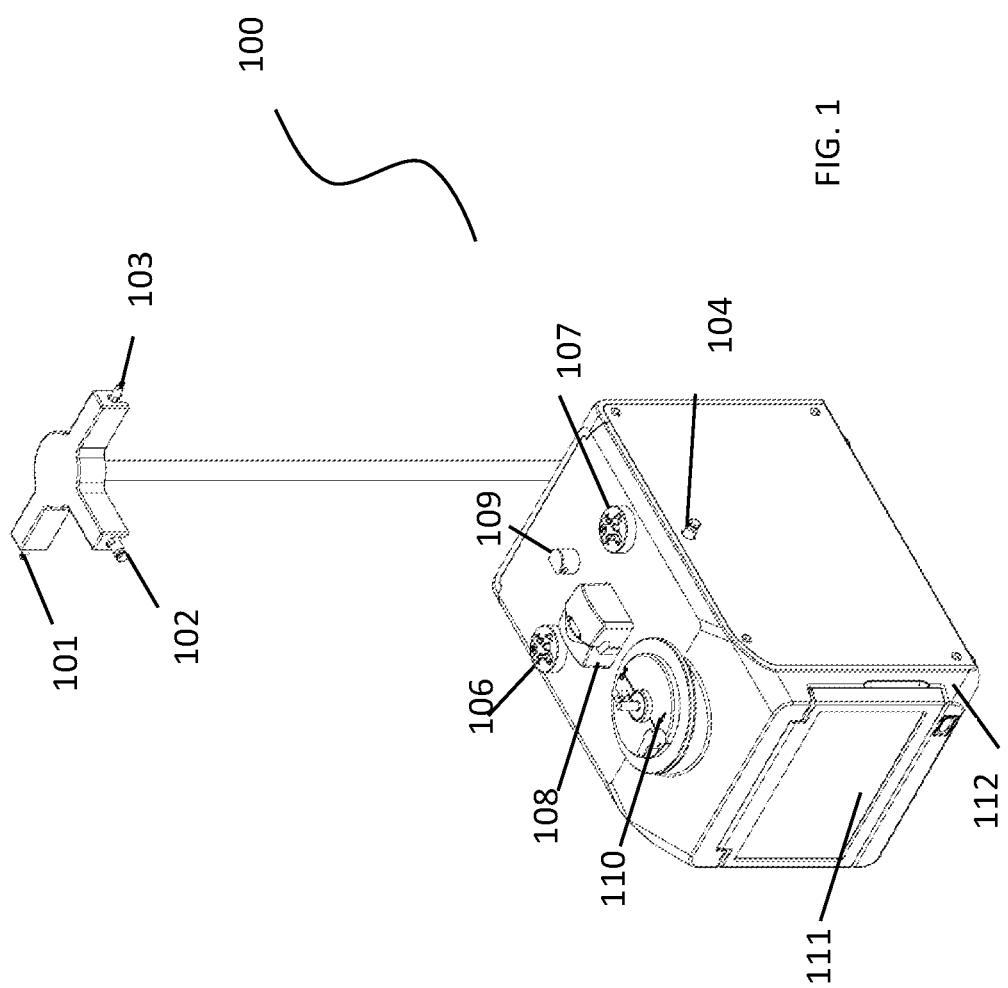
FIG. 1 is a front perspective view of a cabinet for receiving a device for processing cell-containing liquid samples according to an embodiment of the present disclosure.

The present disclosure will now be described more fully hereinafter with reference to the accompanying drawings, in which exemplary embodiments of the present disclosure are shown. The present disclosure may, however, be embodied in many different forms and should not be construed as limited to the embodiments set forth herein. Rather, these embodiments are provided so that the present disclosure is thorough and complete, and will fully convey the scope of the present disclosure to those skilled in the art. Like reference numerals refer to like elements throughout.

The terms used in this specification generally have their ordinary meanings in the art, within the context of the present disclosure, and in the specific context where each term is used. Certain terms that are used to describe the present disclosure are discussed below, or elsewhere in the specification, to provide additional guidance to the practitioner regarding the description of the present disclosure. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It is appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the present disclosure or of any exemplified term. Likewise, the present disclosure is not limited to various embodiments given in this specification.

It is understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It is understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present disclosure.

It is understood that when an element is referred to as being "on," "gathered" to, "connected" to, "coupled" with, "contacting," etc., another element, it can be directly on, gathered to, connected to, coupled with or contacting the other element or intervening elements may also be present. In contrast, when an element is referred to as being, for example, "directly on," "directly gathered" to, "directly connected" to, "directly coupled" with or "directly contacting" another element, there are no intervening elements present. It is also appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the present disclosure. As used herein, the singular forms "a," "an," and "the" are intended to include the plural forms as well, unless the context clearly indicates otherwise. It is further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It is understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present disclosure belongs. It is further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the present disclosure.

Embodiments of the present disclosure are illustrated in detail hereinafter with reference to accompanying drawings. It should be understood that specific embodiments described herein are merely intended to explain the present disclosure, but not intended to limit the present disclosure.

The present disclosure presents a method for processing biological fluids, so that cells in the biological fluids can be easily distributed onto the side walls of a processing chamber under the centrifugation force. The waste liquid or the separated components can be extracted through a tube disposed in the center position of the processing chamber to achieve the purpose of cell concentration. Compared with the prior arts, the present disclosure has the following advantages:

1. Processing duration is reduced and separation efficiency is improved by using a continuous flow centrifugation mechanism.

2. Biological fluids are directly guided to the side wall of the processing chamber by using a flow guide in a centrifugal processing chamber, and the cells can be easily distributed onto the sidewall of the centrifugal processing chamber under the centrifugation force.

Compared with systems without a flow guide, the centrifugation duration can be reduced, the speed of biological fluids flow in and out of the system can be increased greatly, and thus the whole operation duration is reduced and the processing efficiency is improved.

Biological fluids are continuously pumped and separated from the initial volume connected to the inlet port of the centrifugal processing chamber, by being centrifuged in the centrifugal processing chamber in rotation, and finally with supernatant being removed from the central axis of the centrifugal processing chamber and redirected to the waste bag through the outlet port. During the entire separation process, biological cells will remain in the centrifugal processing chamber, and supernatant is continuously removed by a pump.

Figure 2:
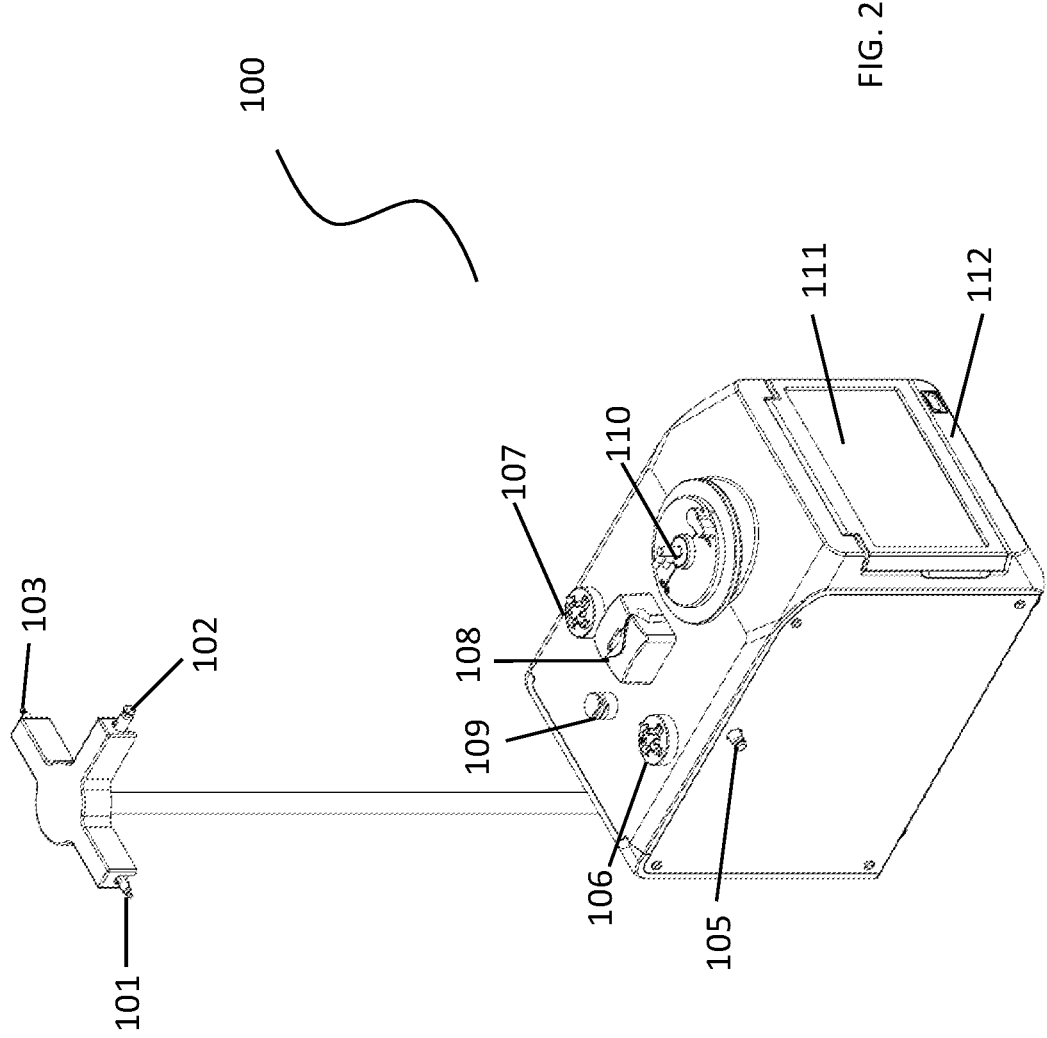
FIG. 2 is a left side perspective view of the cabinet in FIG. 1.
Figure 3:
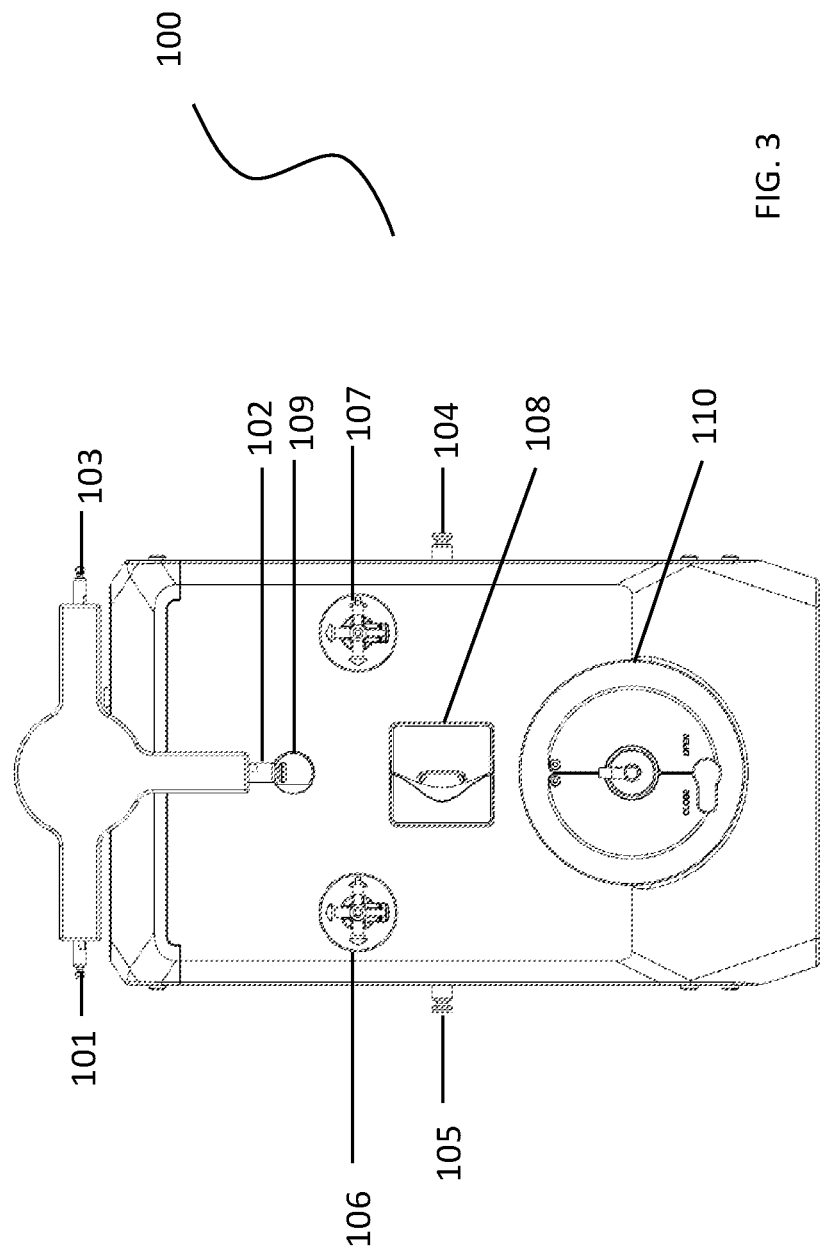
FIG. 3 is a top view of the cabinet in FIG. 1.
Figure 4:
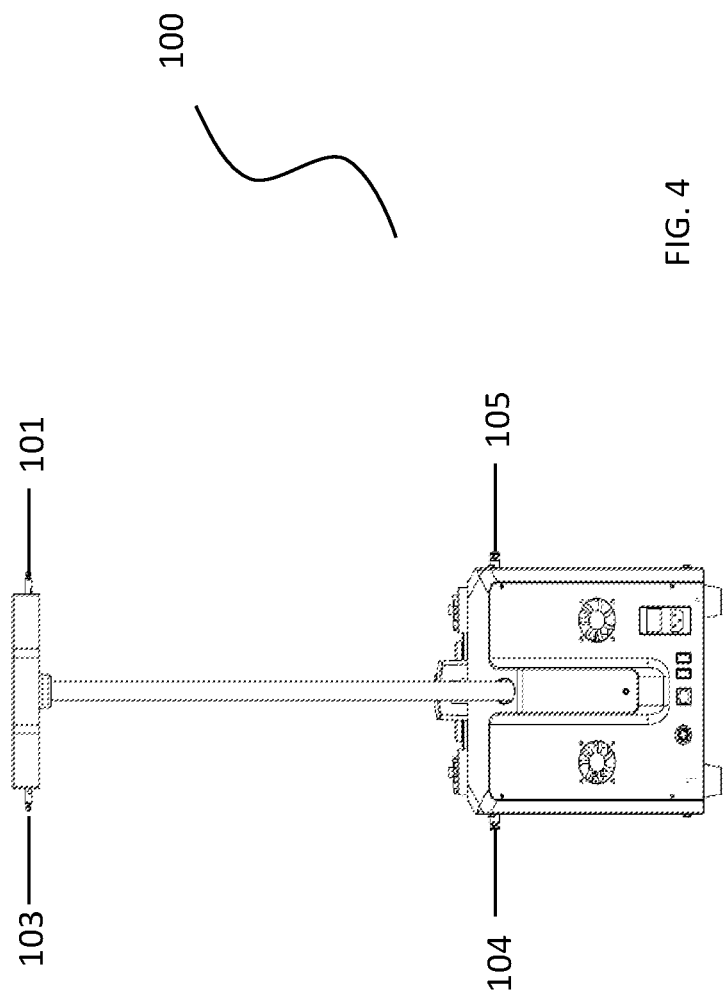
FIG. 4 is a rear view of the cabinet in FIG. 1.

FIG. 1 is a front perspective view of a cabinet for receiving a device for processing cell-containing liquid samples according to an embodiment of the present disclosure. FIG. 2 is a left side perspective view of the cabinet in FIG. 1. FIG. 3 is a top view of the cabinet in FIG. 1. FIG. 4 is a rear view of the cabinet in FIG. 1.

In one embodiment, referring to FIGS. 1-4, a cabinet 100 for receiving a device for processing cell-containing liquid samples includes weight sensors 101, 102, 103, 104 and 105. Cabinet 100 further includes rotatable three-way valves 106 and 107 that are part of the pipeline control system. Cabinet 100 further includes a peristaltic pump 108 and a pipeline ventilation control valve 109, which are part of the pipeline control system, a device for processing cell-containing liquid samples 110, an interface and a control system 111 and a power switch 112.

Figure 5:
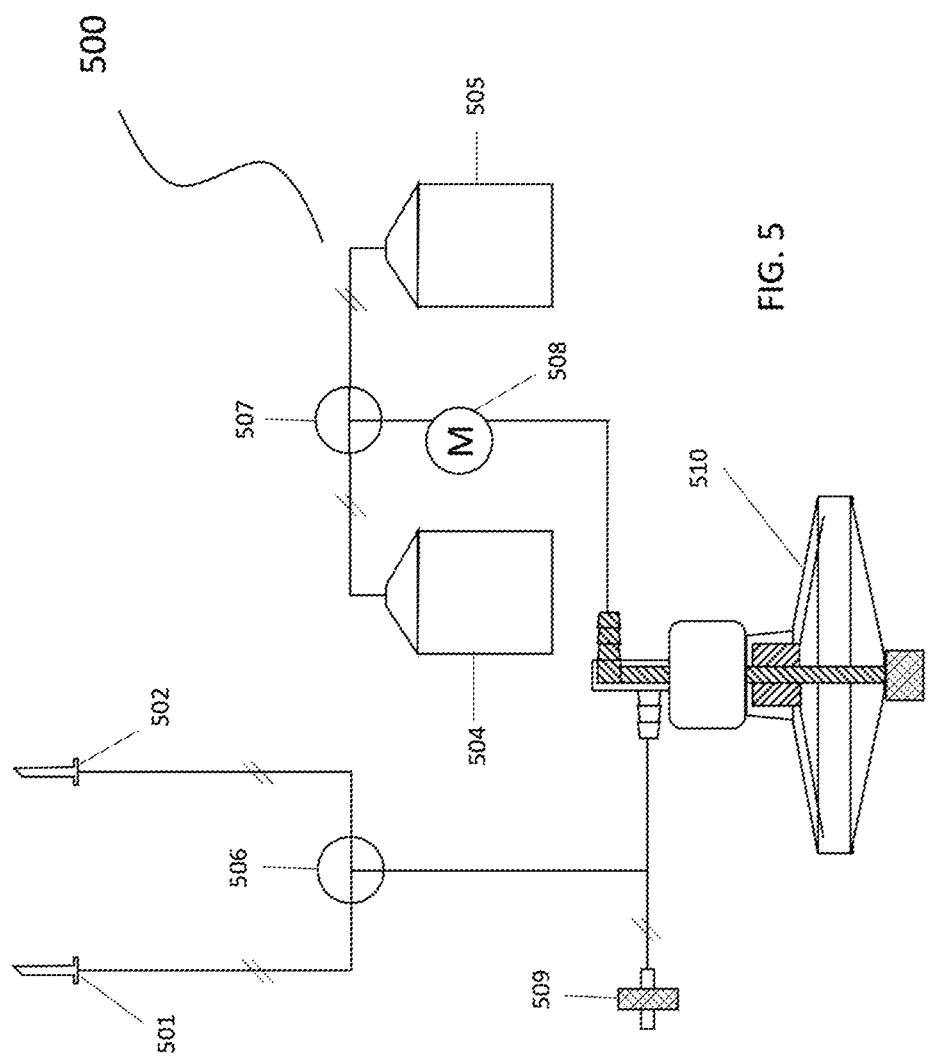
FIG. 5 is a schematic diagram of an example disposable set including a device for processing cell-containing liquid samples according to an embodiment of the present disclosure.

FIG. 5 is a schematic diagram of an example disposable set including a device for processing cell-containing liquid samples according to an embodiment of the present disclosure.

Referring to FIG. 5, schematic diagram 500 of an example disposable set includes connectors 501 and 502, storage bags 504 and 505, pipeline valves 506 and 507, a fluid driving device 508, a connection device 509 and a device for processing cell-containing liquid samples 510. In one example, connectors 501 and 502 may include connectors that connect to one or more fluid storage bags. In one example, connector 501 connects to a fluid storage bag with biological fluids to be processed.

In another example, connector 502 connects to a fluid storage bag with a washing solution. Storage bags 504 and 505 may storage one or more fluids. In one example, storage bag 504 stores the cells after processing the biological fluids. In another example, storage bag 505 stores the separated biological fluid components to be discarded.

In another example, pipeline valves 506 and 507 may include three-way valves. In some examples, fluid driving device 508 may include a pump. In one example, connection device 509 may include a peristaltic pump 108.

Specifically, the device for processing cell-containing liquid samples 510 may comprise at least an inlet and an outlet, a tube, one or more seals, a bearing, a flow guide, and a centrifugal processing chamber.

Figure 6:
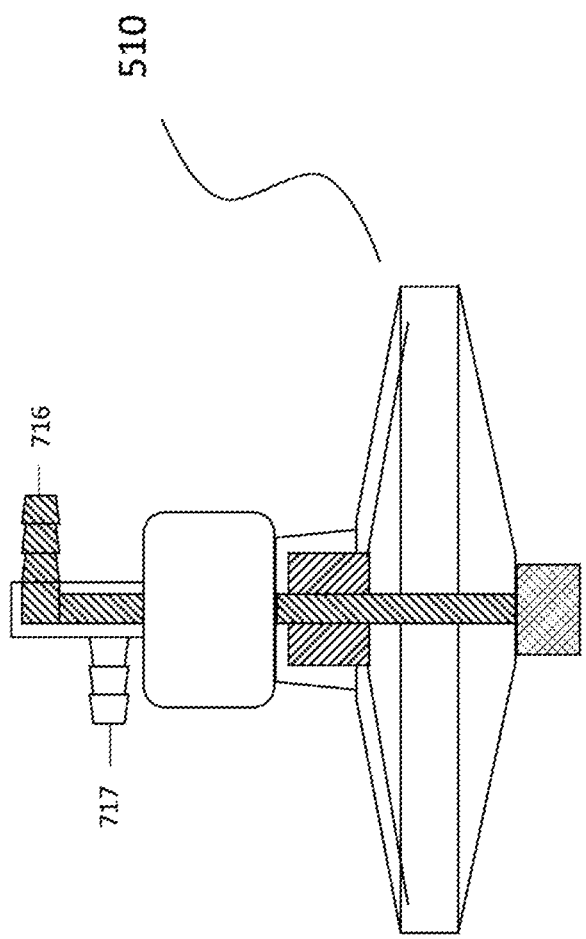
FIG. 6 is a schematic diagram of a device for processing cell-containing liquid samples according to an embodiment of the present disclosure.

FIG. 6 is a schematic diagram of a device for processing cell-containing liquid samples according to an embodiment of the present disclosure. In FIG. 6, the device for processing cell-containing liquid samples 510 comprises: an inlet 717 and an outlet 716.

FIG. 7A is a cross-sectional view of the device for processing cell-containing liquid samples as shown in FIG. 6 according to one embodiment of the present disclosure.

Specifically, FIG. 7A shows a cross-sectional view of the device for processing cell-containing liquid samples 510. In one embodiment, the device for processing cell-containing liquid samples 510 has a connector 711, a cap 712, a tube 718, one or more seal rings 720, one or more rotary dynamic seals 719, a socket 721, a bearing 723, a location stop sleeve 724, an inner dynamic seal disc 726, a centrifugal processing chamber 729, a flow guide 728, a seal 734, and a part 780.

The device for processing cell-containing liquid samples 510 includes a stationary part and a rotatable part. In one example, the stationary part may include tube 718, cap 712, one or more seal rings 720, location stop sleeve 724, and socket 721. The rotatable part may include one or more rotary dynamic seals 719, an inner dynamic seal disc 726, flow guide 728, and centrifugal processing chamber 729.

Cap 712 includes an inlet 717 connected directly or through a connector (adaptor) to intake a liquid sample containing cells to be processed. Cap 712 includes an outlet 716 connected directly or through a connector (adaptor) to output the processed liquid. The upper end of tube 718 is inserted in and fixed to outlet 716, by binding agent or interference fit. In one example, cap 712 and socket 721 are connected by interference fit, and sealed by one or more seal rings 720.

Bearing 723 is a bearing connecting the stationary part with the rotatable part. The stationary part and the rotatable part are connected by one or more seals, for example, by one or more rotary dynamic seals 719, such as by elastic joint, allowing rotation of the rotatable part relative to the stationary part.

Inner dynamic seal disc 726 is provided inside a central hollow protrusion part of centrifugal processing chamber 729. Inner dynamic seal disc 726 is connected with location stop sleeve 724 by a rotary dynamic seal 719. Location stop sleeve 724 may be fixed on the outside wall of tube 718 by a binding agent or tight fit.

Centrifugal processing chamber 729 includes an upper wall 727, a neck extending upward from the upper wall 727, a sidewall 732 and a bottom wall 736. In one example, the neck includes an upper neck 750 and a lower neck 752. The lower neck 752 is located between the upper neck 750 and the upper wall 727. In one example, bottom wall 736 is an inclined wall tilting downwardly. In one example, centrifugal processing chamber 729 includes an upper part 740 and a lower part 742. The upper part 740 includes the neck, upper wall 727 and sidewall 732. As shown in FIG. 7A, side wall 732 is a part of the upper part 740. In another example, side wall 732 may be a part of the lower part 742. In one example, centrifugal processing chamber 729 may be rotational symmetric in a shape of cylinder, polygon or discus.

The lower part 742 includes bottom wall 736. In one example, the upper part 740 and the lower part 742 are connected by fastener or heat seal connection, and preferably sealed by a seal 734. In one example, upper wall 727 and the part of the flow guide 728 in proximity to the upper wall 727 may be horizontal or inclined upwardly as shown in FIG. 7A. A lowest point 770 is formed in the middle of the bottom wall 736. Thus, fluids in the centrifugal processing chamber 729 may be guided to the lowest point 770 due to gravity.

A part for connecting a centrifugal driving device may be provided on the bottom of the centrifugal processing chamber 729, enabling the rotation of the centrifugal processing chamber 729 driven by the centrifugal driving device. For example, as shown in FIG. 7A, the part 780 for connecting a centrifugal driving device may be a protrusion extending downward from the central of the bottom of the centrifugal processing chamber 729.

Flow guide 728 is designed for guiding the liquid sample, for example, to sidewall 732 of the centrifugal processing chamber 729. Flow guide 728 may be inserted in and coaxially rotatable with the centrifugal processing chamber 729. Flow guide 728 may, for example, include an inclined frusto-conical upper surface with a hole in the center which is sized and shaped to fit the tube 718. The frusto-conical upper surface is in proximity to but not contact with the upper wall 727. Flow guide 728 may include an upwardly-protruding central part. The upwardly-protruding central part is hollow and is connected to and sized and shaped to fit the center hole of the flow guide 728. Connection or fixation of the flow guide 728 and the centrifugal processing chamber 729 may be achieved by using one or more protrusions provided on the outside wall of the upwardly-protruding central part and against the inner wall of the lower neck 752 of centrifugal processing chamber 729, by for example, tight fit or a binding agent (referring to FIGS. 9, 10, 11(a), 11(b)). In FIG. 7A which is a cross-sectional view taken through gaps between the protrusions on the upwardly-protruding central part, a small spacing is shown between the central part of flow guide 738 and the lower neck 752 (referring to FIGS. 9, 10, 11(a), 11(b)).

The upper end of tube 718 is connected to outlet 716. The lower end of tube 718 is in proximity (as close as possible) to but not in contact with the lowest point 770, allowing that the liquid guided to the lowest point 770 can be removed from the centrifugal processing chamber 729.

A first fluid passage 760 is defined by the space between cap 712 and tube 718. A second fluid passage 762 is defined by the space between the upper neck 750 and tube 718. A third fluid passage 764 is defined by the space between the lower neck 752 and tube 718. A fourth fluid passage 766 is defined by the upper wall 727 and flow guide 728. A liquid sample containing cells flows from inlet 717 and through first fluid passage 760, second fluid passage 762, third fluid passage 764, and fourth fluid passage 766 in order. Flow guide 728 is in proximity to but not in contact with the sidewall 732. Flow guide 728 guides the fluids passing through first fluid passage 760, second fluid passage 762, third fluid passage 764, and fourth fluid passage 766 to sidewall 732.

FIG. 7B is a cross-sectional view of the device for processing cell-containing liquid samples as shown in FIG. 6 according to another embodiment of the present disclosure.

As described above, flow guide 728 is connected to the lower neck 752 of centrifugal processing chamber 729 using the protrusions, by for example, tight fit or a binding agent. In FIG. 7B which is a cross-sectional view taken through the protrusions (not the gaps therebetween) on the upwardly-protruding central part of flow guide 728, no spacing is showed between the upwardly-protruding central part of flow guide 728 and the lower neck 752 (referring to FIGS. 9, 10, 11(a), 11(b)).

The principle of the design is that a liquid sample containing cells is guided by flow guide 728 to the sidewall 732 of the centrifugal processing chamber 729 in rotation. In one example, the centrifugal force at the side of the centrifugal processing chamber 729 is much greater than the centrifugal force in the middle of the centrifugal processing chamber 729.

Biological cells are separated from supernatant or other medium, by a density physical principle after being exposed to a horizontal sedimentation force. Cells remain compacted at the inside wall of the centrifugal processing chamber 729 including, sidewall 732, while the separated fluid to be discarded is removed through tube 718 in the middle of the centrifugal processing chamber 729 and outlet 716.

In one example, device for processing cell-containing liquid samples 510 is designed for continuous intake of a liquid sample containing cells and continuous removal of separated waste. The cells remain compacted at the inside wall of centrifugal processing chamber 729, to achieve the purpose of cell concentration.

Flow guide 728 is configured to guide the liquid sample to the sidewall 732 of centrifugal processing chamber 729. In contrast, if the liquid sample flows in centrifugal processing chamber 729 from the central axis of device for processing cell-containing liquid samples 510, it will take a long time for the cells in the liquid sample to be distributed to sidewall 732 of centrifugal processing chamber 729 under the centrifugal force. As a result, if the flow rate of the liquid sample is increased, the cells in the liquid sample may not have sufficient time to travel to the inside wall of centrifugal processing chamber 729 and may be extracted out of centrifugal processing chamber 729, resulting in a low cells recovery rate. In the present disclosure, the liquid sample containing cells directly reaches the sidewall 732 of centrifugal processing chamber 729, so that the cells can be easily distributed to the sidewall 732 of centrifugal processing chamber 729 under the centrifugal force. Therefore, in the present disclosure, the centrifugation duration may be reduced and a high cell recovery rate under high flow rates may be achieved.

Figure 8:
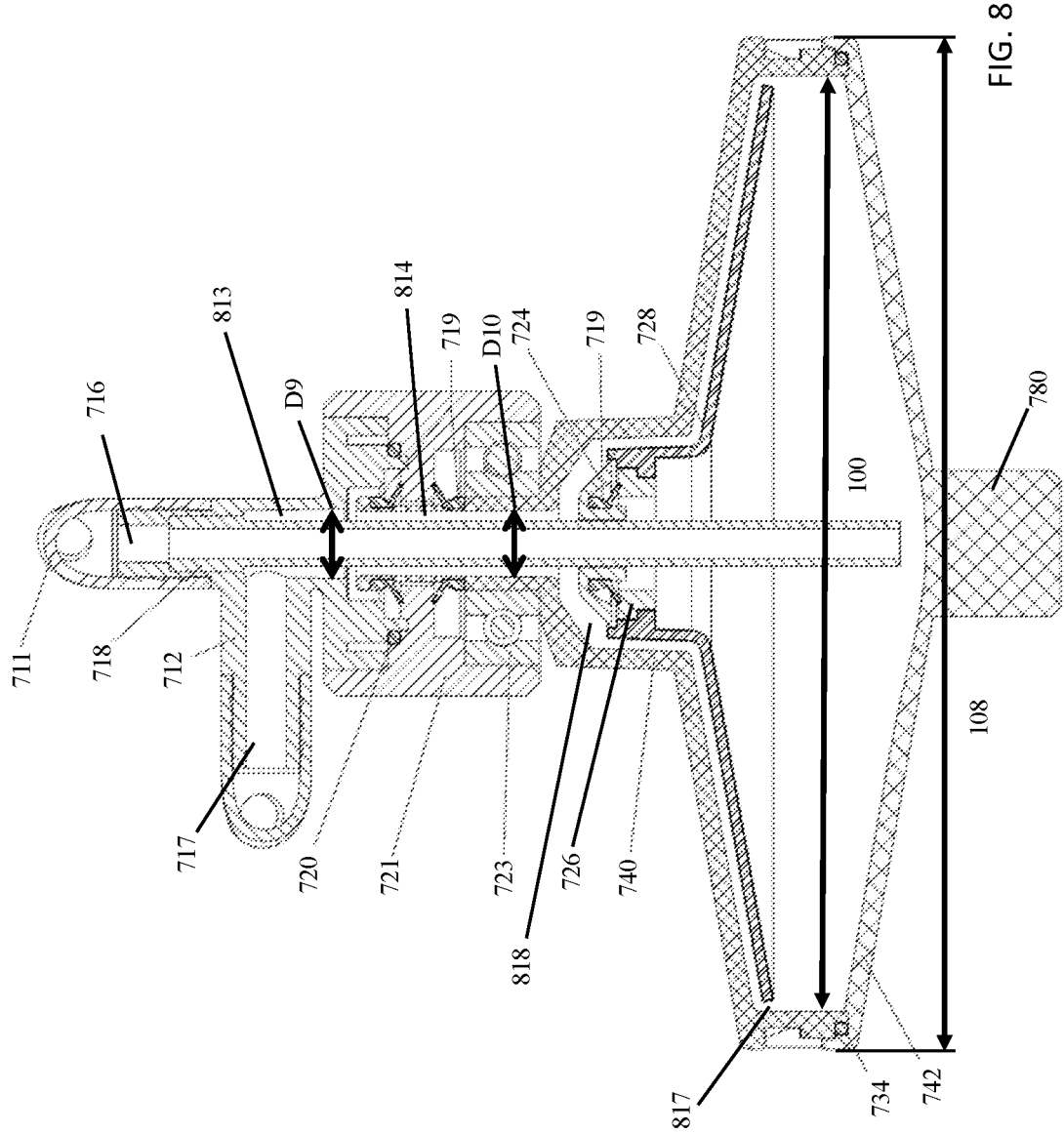
FIG. 8 is a cross-sectional view of the device for processing cell-containing liquid samples as shown in FIG. 6.

FIG. 8 is a cross-sectional view of the device for processing cell-containing liquid samples as shown in FIG. 6.

Exemplary dimensions of the device, and speed and flux of the liquid sample associated with corresponding areas of the device 510 are illustrated in table 1 below. These dimensions, speed, and flux are provided only as examples but in no way as a limitation to the present disclosure.

TABLE 1

Exemplary dimensions of the device, and speed and flux of the liquid sample associated with corresponding areas of the device 510.

| Area | cross section (mm$^2$) | speed (mm/s) | flux (ml/min) |
| --- | --- | --- | --- |
| 717 | 14.52 | 229.56 | 200 |
| 813 | 11.54 | 288.85 | 200 |
| 814 | 12.53 | 266.03 | 200 |
| 718 | 8.04 | 414.6 | 200 |
| 716 | 12.57 | 265.2 | 200 |
| 817 | 7696.9 | 0.44 | 200 |
| 818 | 69.55 | 47.9 | 200 |

In one example, the speed of a liquid sample associated with corresponding areas of device for processing cell-containing liquid samples 510 refers to the speed of the liquid sample going through the corresponding areas of device for processing cell-containing liquid samples 510. In one example, the flux of a liquid sample associated with corresponding areas of device for processing cell-containing liquid samples 510 refers to the flux of the liquid sample going through the corresponding areas of device for processing cell-containing liquid samples 510.

Figure 7:
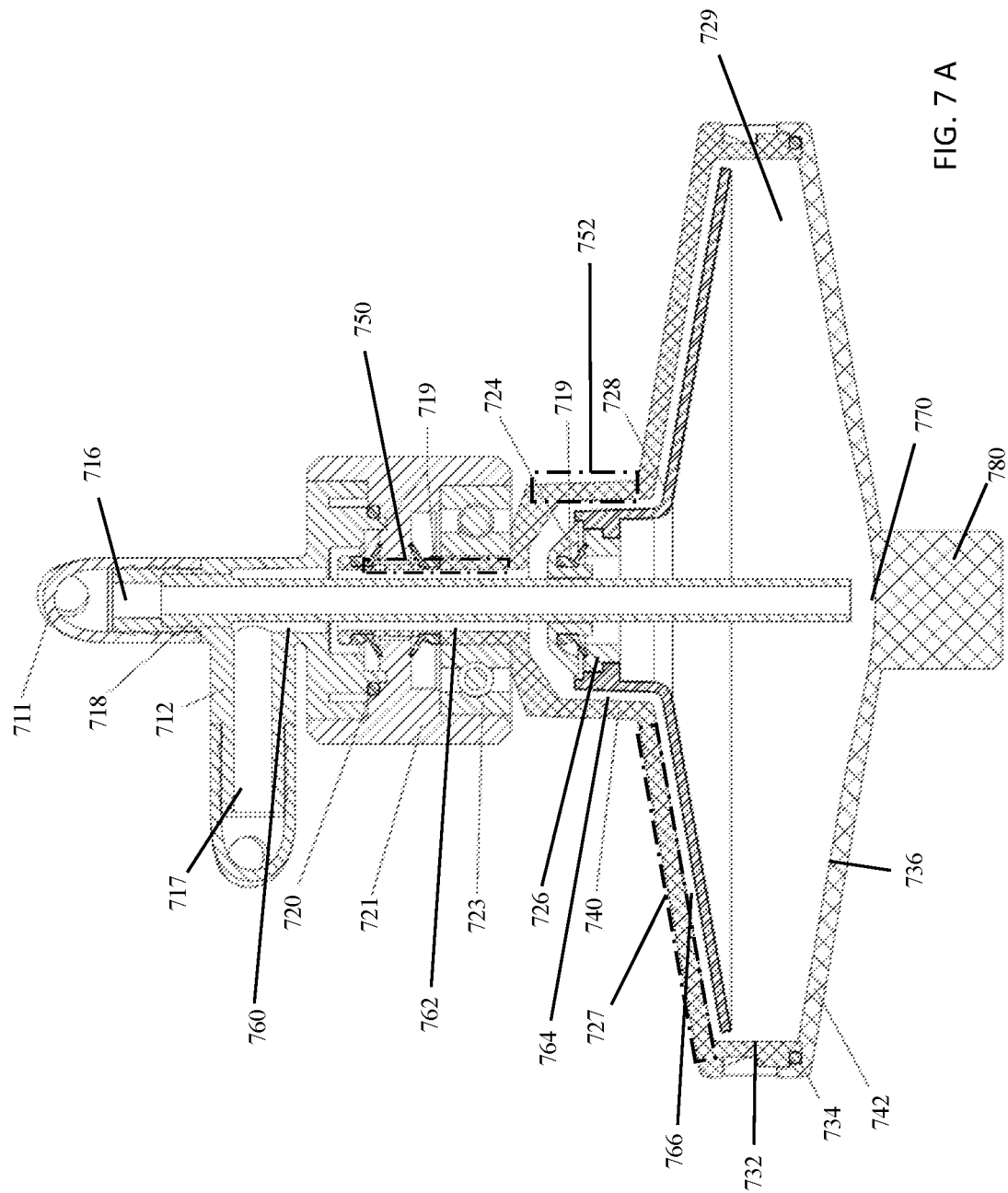
FIG. 7A is a cross-sectional view of the device for processing cell-containing liquid samples as shown in FIG. 6 according to one embodiment of the present disclosure.
FIG. 7B is a cross-sectional view of the device for processing cell-containing liquid samples as shown in FIG. 6 according to another embodiment of the present disclosure.
Figure 7:
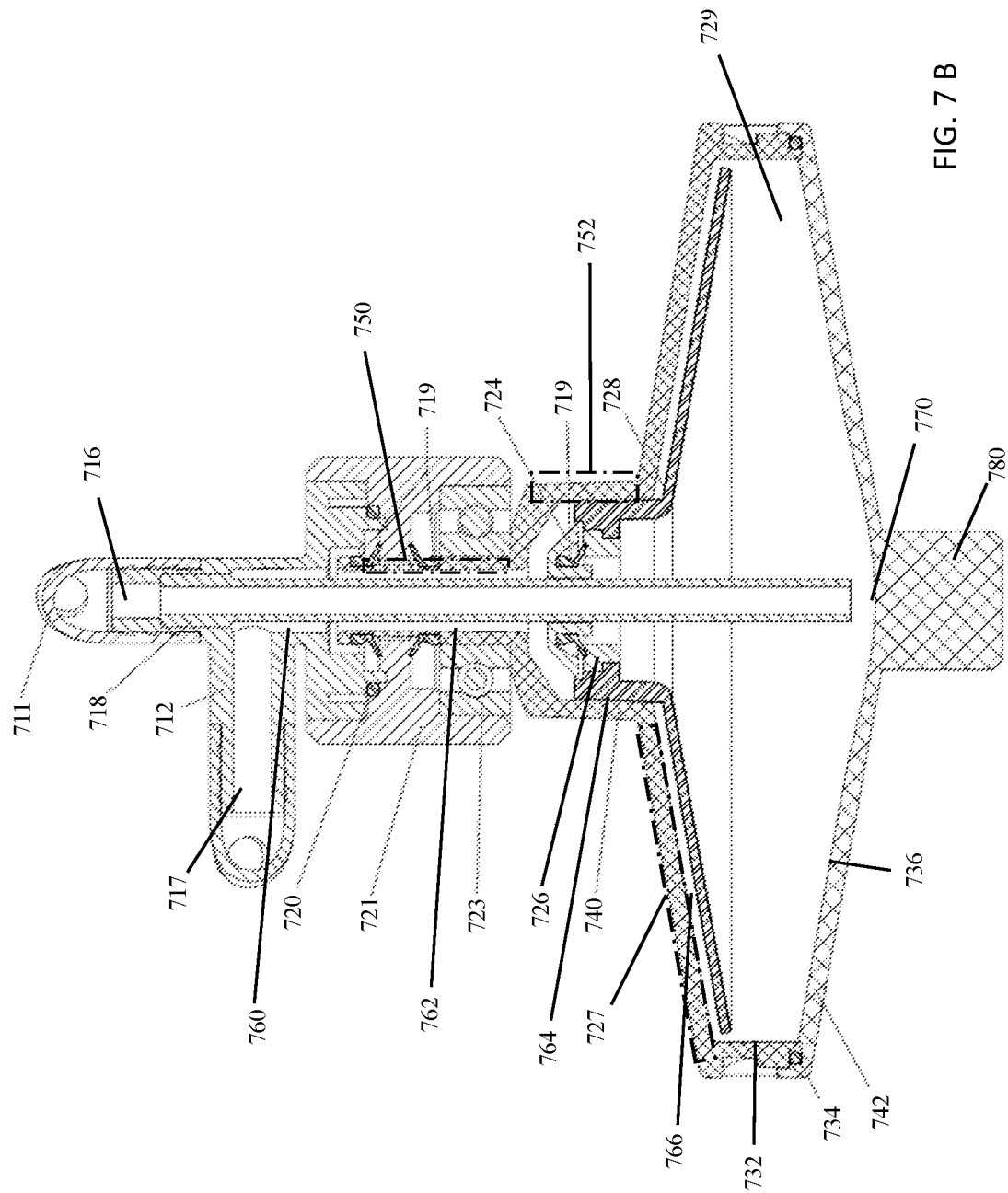

In FIG. 8, inlet 717, outlet 716, and tube 718 are as described in details with reference to FIG. 7A. Space 813 is a space between cap 712 and tube 718. Space 814 is a space between the upper neck 750 and tube 718. Space 818 is a space between the lower neck 752 and tube 718. Space 817 is a space between the upper wall 727 and the flow guide 728. With reference to FIGS. 7-8, a liquid sample containing cells is received by centrifugal processing chamber 729 through inlet 717, space 813, space 814, space 818, and space 817 in sequence. In one example, the inner diameter of tube 718 is greater than 2 mm to achieve a good processing efficiency. In one embodiment, D9 as shown in FIG. 8 is about 6.8 mm. In one embodiment, D10 as shown in FIG. 8 is about 7.2 mm. In one embodiment, 100 as shown in FIG. 8 is about 99.4 mm. In one embodiment, 108 as shown in FIG. 8 is about 98 mm.

However, an ordinary skill in the art understands that the present disclosure is not limited to the above-mentioned dimensions. Other dimensions can be utilized in the apparatus of the present disclosure. The dimensions are utilized as exemplary illustrations of the present disclosure.

Figure 9:
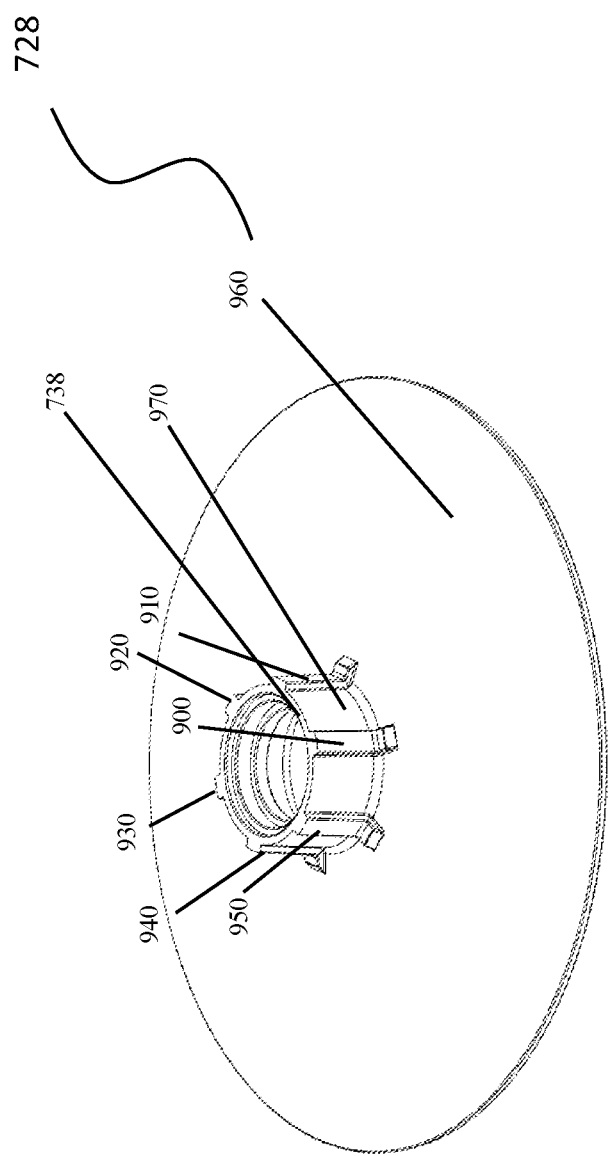
FIG. 9 is a perspective view of a flow guide of the device for processing cell-containing liquid samples as shown in FIG. 6.
Figure 10:
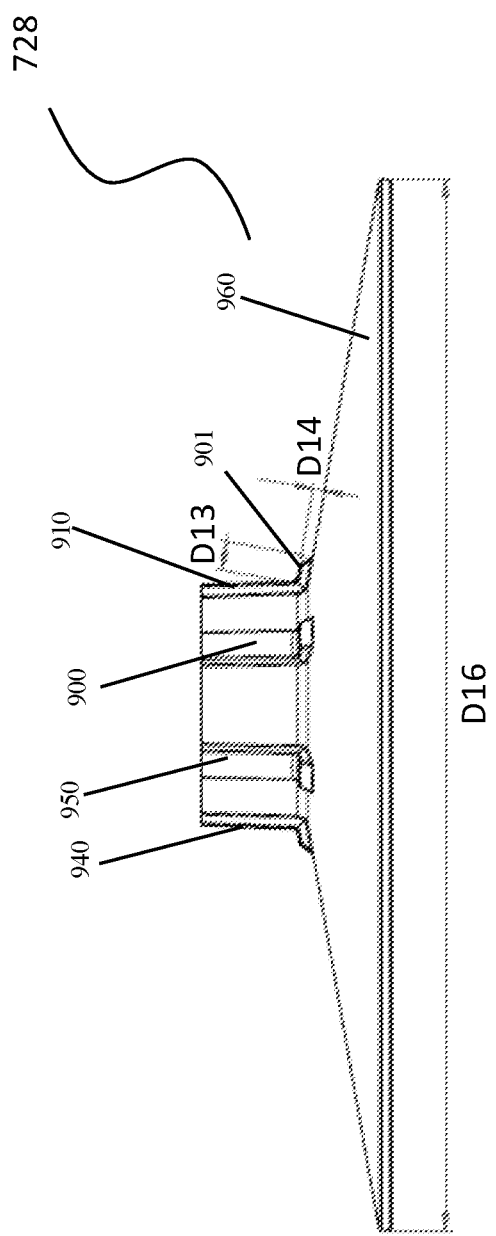
FIG. 10 is a side view of the flow guide as shown in FIG. 9.

FIG. 9 is a perspective view of the flow guide of the device as shown in FIG. 6. FIG. 10 is a side view of the flow guide as shown in FIG. 9. FIG. 11(a) is a plan view of the flow guide as shown in FIG. 9. FIG. 11(b) is a cross-sectional view of the flow guide as shown in FIG. 9.

Referring to FIGS. 9, 10, 11(a), 11(b), flow guide 728 has an inclined frusto-conical upper surface 960 (flow guide 728 may also have a horizontal configuration rather than "inclined" as shown in Figures), a central part 738, and six protrusions 900, 910, 920, 930, 940 and 950 provided on the central part 738. The number of the protrusions on the flow guide 728 may not be limited to six, and can be one, two, three, four, five or any number. The protrusion(s) may have any shape including bar, cube, dots, ring, and so on. The protrusion(s) may extend from the central part 738 to the upper surface 960. In one example, the protrusion 910 includes a bottom member 901. In one example, the length D13 of the bottom member 901 as shown in FIG. 10 can be from 2.7 mm to 37 mm. In one example, the height D14 of the bottom member 901 as shown in FIG. 10 may be about 1.1 mm. In one example, the width D15 of protrusion 900 may be about 3.4 mm. The liquid sample containing cells may flow through the gaps 970 between the adjacent protrusions. In one example, the diameter D16 of flow guide 728 as shown in FIG. 10 may be about 98 mm.

However, an ordinary skill in the art understands that the present disclosure is not limited to the specific above-mentioned dimensions or configurations. Other dimensions or configurations can be utilized in the apparatus of the present disclosure. The dimensions or configurations are utilized as exemplary illustrations of the present disclosure.

Figure 12B:
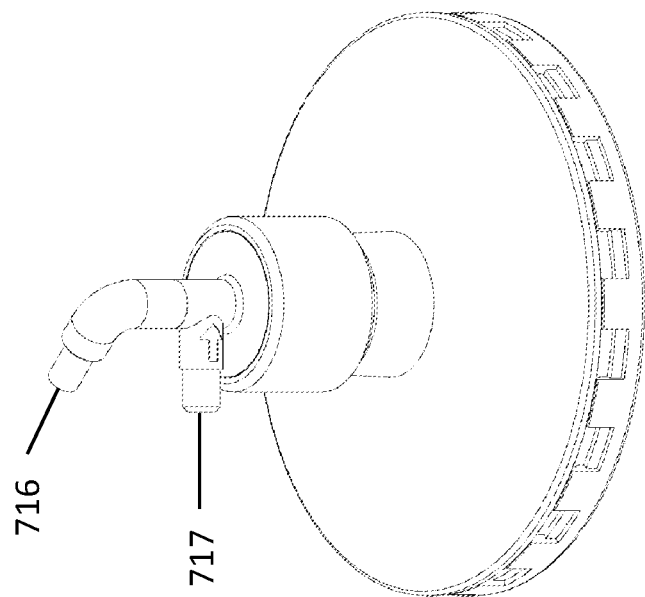
FIG. 12(*a*) is a front side view of the inlet and the outlet of the device for processing cell-containing liquid samples as shown in FIG. 6.
Figure 12A:
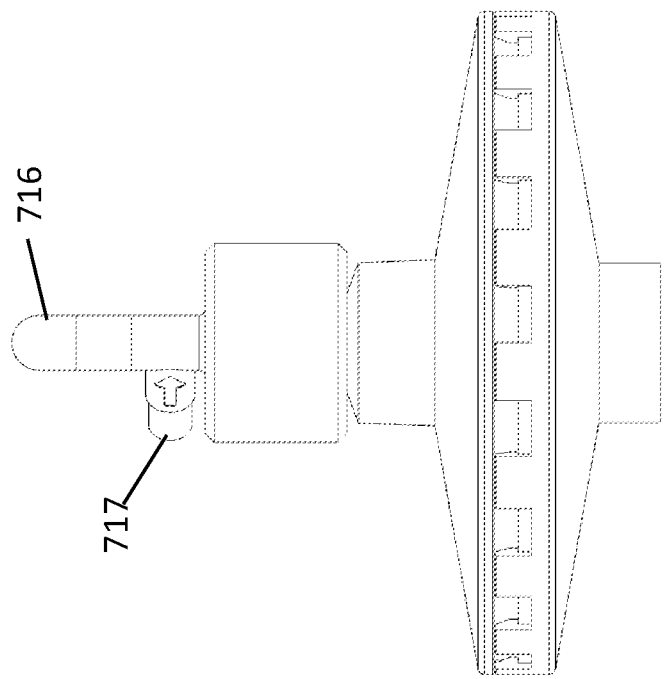

FIG. 12(a) is a front side view of the inlet and the outlet of the device for processing cell-containing liquid samples as shown in FIG. 6.

FIG. 12(b) is a perspective view of the inlet and the outlet of the device for processing cell-containing liquid samples as shown in FIG. 6.

Figure 13:
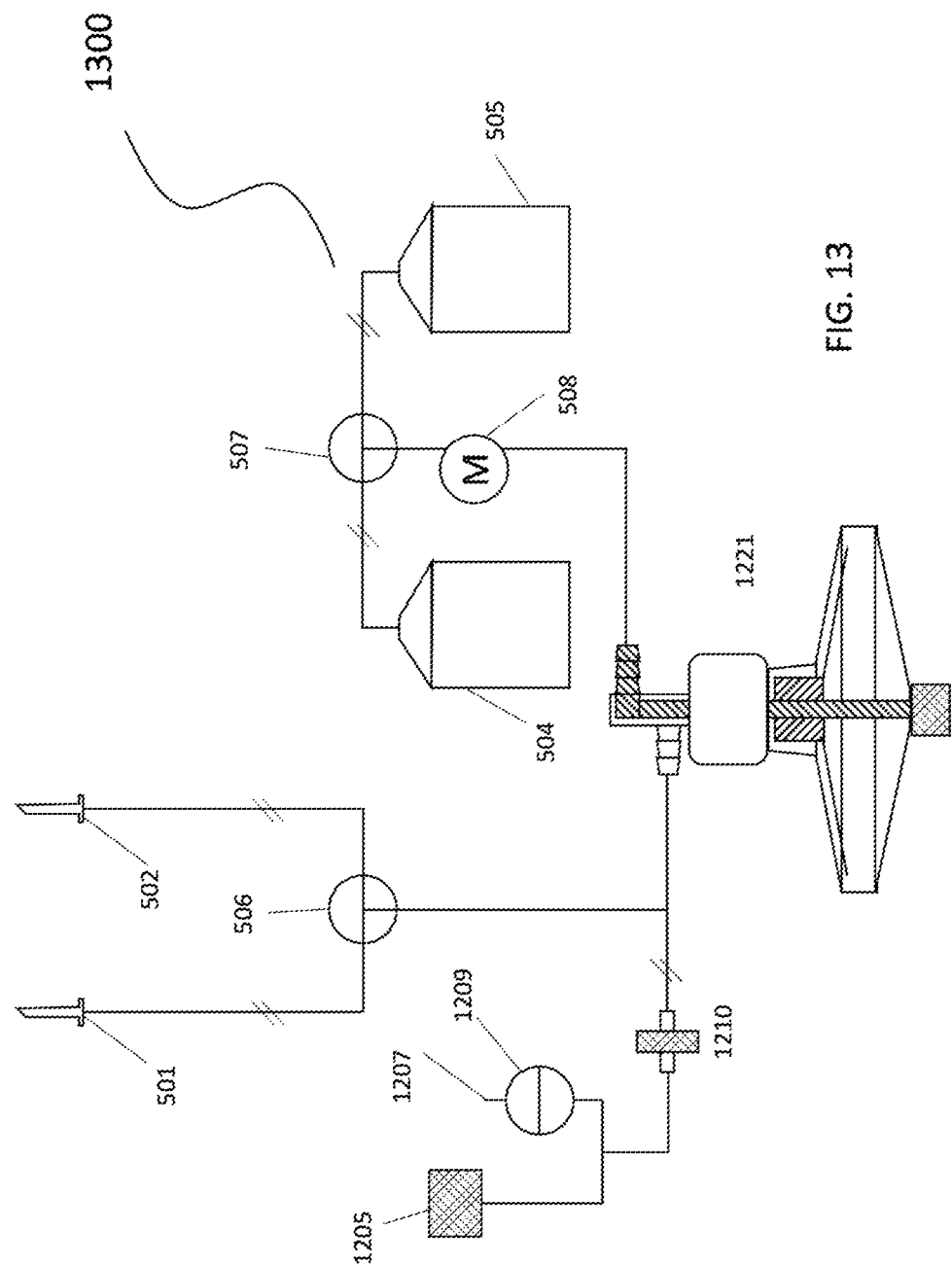
FIG. 13 is a schematic diagram of an example disposable set including a device for processing cell-containing liquid samples according to another embodiment of the present disclosure.

FIG. 13 is a schematic diagram 1300 of an example disposable set including a device for processing cell-containing liquid samples according to another embodiment of the present disclosure.

Referring to FIG. 13, the example disposable set includes connectors 501 and 502, storage bags 504 and 505, pipeline valves 506 and 507, a fluid driving device 508, to be used with device for processing cell-containing liquid samples 510. In one example, connectors 501 and 502 may include connectors that connect to one or more fluid storage bags. Storage bags 504 and 505 may storage one or more fluids.

In one example, connector 501 connects to a fluid storage bag with the liquid sample to be processed. In another example, connector 502 connects to a fluid storage bag with a washing solution. Storage bags 504 and 505 may storage one or more fluids. In one example, storage bag 504 stores the final solution containing target cells. In another example, storage bag 505 stores the waste to be discarded.

In another example, pipeline valves 506 and 507 may include three-way valves. In some examples, fluid driving device 508 may include a pump.

Device for processing cell-containing liquid samples 510 comprises: an inlet and an outlet, a tube, one or more rotary seals, a bearing, a flow guide, and a centrifugal processing chamber.

The schematic diagram 1300 further includes pressure sensor 1205, a gas supply 1207 controlled by a control switch 1209 that is switched off by default and controls the gas flow of gas supply 1207.

The example disposable set may be operated in accordance with the steps as described below:

1. A sample bag is connected to a sterile connector 501. Saline or washing solution bag is connected to a sterile connector 502.

2. One or more disposable sets are connected in sequence as shown in FIG. 13.

3. Device for processing cell-containing liquid samples 510 is turned to run one or more programs.

4. Centrifugation is started. A liquid sample containing cells is received by device for processing cell-containing liquid samples 510 from the inlet. Cells are distributed to the inside wall of centrifugal processing chamber 729 under the centrifugation force. The waste to be discarded is extracted into storage bag 504. In one example, fluid driving device 508 is turned on to pump the waste to be discarded from outlet 716 and tube 718. The liquid sample may be processed continuously until all the sample is processed.

5. Under the centrifugation operation, the inlet of device for processing cell-containing liquid samples 510 is switched to saline or washing solution, a certain amount of saline or washing solution is pumped into the device for processing cell-containing liquid samples 510. This may be an optional step which can be skipped.

6. Centrifugation is stopped. Centrifugal processing chamber 729 is configured to rotate clockwise and counter-clockwise, to mix cells remaining in the centrifugal processing chamber 729 with a suspension solution filled in the centrifugal processing chamber 729 after the centrifugation more consistently, resulting a final solution containing target cells.

7. Outlet of device for processing cell-containing liquid samples 510 is switched to connect to storage bag 505.

8. Control switch 1209 is switched to connect to gas supply 1207.

9. The final solution containing target cells are extracted to storage bag 505, and control switch 1209 is switched off.

10. Saline or washing solution is pumped into and filled in centrifugal processing chamber 729. Centrifugal processing chamber 729 is configured to rotate in a clockwise and a counter clockwise direction for rinsing centrifugal processing chamber 729. The fluid in centrifugal processing chamber 729 is extracted to storage bag 505, and this step may be repeated one or more times.

In one embodiment, the pump can be any pump in different formats as long as the separated component, the fluid can be extracted through tube 718.

In one embodiment, tube 718 is not rotatable or moveable inside centrifugal processing chamber 729, and is coupled to inlet 717 and outlet 716.

The foregoing description of the exemplary embodiments of the present disclosure has been presented only for the purposes of illustration and description and is not intended to be exhaustive or to limit the present disclosure to the precise forms disclosed. Many modifications and variations are possible in light of the above teaching.

The embodiments were chosen and described in order to explain the principles of the present disclosure and their practical application so as to activate others skilled in the art to utilize the present disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A device for processing a liquid sample containing cells, comprising:
    a stationary part; and
    a rotatable part,
    wherein the stationary part includes a cap, a socket connected to the cap, and a tube located within the cap and the socket,
    wherein the rotatable part includes a centrifugal processing chamber, and a flow guide located within the centrifugal processing chamber,
    wherein the stationary part and the rotatable part are connected by a plurality of rotary dynamic seals allowing rotation of the rotatable part relative to the stationary part,
    wherein the cap includes a first port connected to an inlet, and a second port connected to an outlet,
    wherein the centrifugal processing chamber includes an upper wall, a neck extending upwardly from the upper wall, a sidewall and a bottom wall tilting downwardly, wherein the neck includes an upper neck and a lower neck, wherein a lowest point is formed in the middle of the bottom wall, so that the liquid in the centrifugal processing chamber is guided to the lowest point due to gravity,
    wherein the flow guide is inserted in and coaxially rotatable with the centrifugal processing chamber during centrifugation, wherein the flow guide is close to but not in contact with the upper wall of the centrifugal processing chamber, wherein the flow guide is sized and shaped to fit the upper wall of the centrifugal processing chamber, wherein the flow guide includes a center hole and the center hole is sized and shaped to fit the tube, and wherein the tube passes through the center hole,
    wherein the upper end of the tube is connected to the outlet, and the lower end of the tube is close to but not in contact with the lowest point, allowing that the liquid guided to the lowest point is removed from the centrifugal processing chamber, and wherein the device is configured to receive the liquid sample from the inlet and guide the liquid sample to flow through a first space between the cap and the tube, a second space between the upper neck and the tube, a third space between the lower neck and the tube, and a fourth space between the upper wall and the flow guide and to the side wall of centrifugal processing chamber in order.

2. The device according to claim 1, wherein the upper end of the tube is fixed at the second port connected to the outlet.

3. The device according to claim 1, further comprising at least one stationary seal.

4. The device according to claim 1, further comprising a bearing connected to both the stationary part and the rotatable part.

5. The device according to claim 1, wherein the flow guide includes a hollow upwardly-protruding central part connected to the center hole, a plurality of protrusions located on the sidewall of the upwardly-protruding central part, and wherein the plurality of protrusions are configured to fix the flow guide inside the lower neck of the centrifugal processing chamber.

6. The device according to claim 5, further comprising an inner dynamic seal disc located inside the upwardly-protruding central part and connected with a location stop sleeve located at the outside wall of the tube by one of the plurality of rotary dynamic seals.

7. The device according to claim 1, wherein a part for connecting a centrifugal driving device is provided on the bottom of the centrifugal processing chamber, enabling the rotation of the centrifugal processing chamber driven by the centrifugal driving device.

8. The device according to claim 1, wherein the centrifugal processing chamber includes an upper part and a lower part connected to the upper part, and wherein the upper part includes the neck, the upper wall and the sidewall and the lower part includes the bottom wall tilting downwardly.

9. The device according to claim 1, wherein the first port is connected to the inlet via a first connector and/or the second port is connected to the outlet via a second connector.

10. The device according to claim 1, wherein the centrifugal processing chamber is rotational symmetric.

11. A system for processing a liquid sample containing cells, comprising:
    the device of claim 1;
    at least one sample bag/washing solution bag;
    at least one collection bag/waste bag; and
    a pipeline system for connecting the at least one sample bag/washing solution bag to the inlet of the device of claim 1 and connecting the at least one collection bag/waste bag to the outlet of the device of claim 1.

12. The system according to claim 11, further comprising a fluid driving device.

13. The system according to claim 12, wherein the fluid driving device includes a first peristaltic pump connected to the inlet and/or a second peristaltic pump connected to the outlet.

14. A method for processing a liquid sample containing cells using the device according to claim 1, the method comprising the following steps:
    inputting the liquid sample to the device of claim 1 via the inlet during a centrifugal rotation of the centrifugal processing chamber; and
    outputting a processed liquid from the device of claim 1 via the tube and the outlet during or after the centrifugal rotation of the centrifugal processing chamber.

15. The method according to claim 14, wherein the inputting and the outputting are simultaneous.

16. The method according to claim 14, further comprising:
    filling the centrifugal processing chamber with a washing solution;
    mixing the washing solution with the cells remaining in the centrifugal processing chamber by rotating the centrifugal processing chamber clockwise and counterclockwise; and
    outputting and collecting a mixture of the cells and the washing solution.

* * * * *